(12) United States Patent
Eidenschink et al.

(10) Patent No.: US 8,470,023 B2
(45) Date of Patent: Jun. 25, 2013

(54) PERCUTANEOUS VALVE, SYSTEM, AND METHOD

(75) Inventors: Tracee E. J. Eidenschink, Wayzata, MN (US); Joseph M. Thielen, Buffalo, MN (US); William J. Drasler, Minnetonka, MN (US); Graig L. Kveen, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 24 days.

(21) Appl. No.: 13/166,150

(22) Filed: Jun. 22, 2011

(65) Prior Publication Data
US 2011/0251678 A1    Oct. 13, 2011

Related U.S. Application Data

(63) Continuation of application No. 12/012,898, filed on Feb. 5, 2008, now Pat. No. 7,967,853.

(60) Provisional application No. 60/899,446, filed on Feb. 5, 2007.

(51) Int. Cl.
*A61F 2/06* (2006.01)

(52) U.S. Cl.
USPC ........ 623/1.24; 623/2.11; 623/2.14; 623/2.17

(58) Field of Classification Search
USPC .................. 623/2.1, 2.12, 2.14, 2.17
See application file for complete search history.

(56) References Cited

U.S. PATENT DOCUMENTS

| | | |
|---|---|---|
| 3,671,979 A | 6/1972 | Moulopoulos |
| 4,291,420 A | 9/1981 | Reul |
| 4,787,901 A | 11/1988 | Baykut |
| 4,872,874 A | 10/1989 | Taheri |
| 4,935,030 A | 6/1990 | Alonso |
| 4,994,077 A | 2/1991 | Dobben |
| 5,002,567 A | 3/1991 | Bona |
| 5,141,491 A | 8/1992 | Bowald |
| 5,163,953 A | 11/1992 | Vince |
| 5,219,355 A | 6/1993 | Parodi |
| 5,254,127 A | 10/1993 | Wholey |
| 5,327,774 A | 7/1994 | Nguyen |
| 5,332,402 A | 7/1994 | Teitelbaum |
| 5,370,685 A | 12/1994 | Stevens |
| 5,411,552 A | 5/1995 | Andersen |
| 5,469,868 A | 11/1995 | Reger |

(Continued)

FOREIGN PATENT DOCUMENTS

| | | |
|---|---|---|
| EP | 0380666 | 8/1990 |
| EP | 0466518 | 1/1992 |

(Continued)

*Primary Examiner* — David H Willse
*Assistant Examiner* — Tiffany Shipmon
(74) *Attorney, Agent, or Firm* — Vidas, Arrett & Steinkraus, P.A.

(57) ABSTRACT

Apparatus, systems, and methods for percutaneous valve replacement and/or augmentation are provided. The apparatus includes a valve having a valve frame, a valve leaflet coupled to the valve frame, and a leaflet transition member coupled to the valve leaflet. The valve leaflet and leaflet transition member can transition from a first position where the valve leaflet and leaflet frame are at least partially outside a lumen of the valve frame to a second position where the valve leaflet and the leaflet transition member are within the lumen of the valve frame.

18 Claims, 5 Drawing Sheets

U.S. PATENT DOCUMENTS

| | | | |
|---|---|---|---|
| 5,480,423 A | 1/1996 | Ravenscroft | |
| 5,500,014 A | 3/1996 | Quijano | |
| 5,545,214 A | 8/1996 | Stevens | |
| 5,554,185 A | 9/1996 | Block | |
| 5,643,208 A | 7/1997 | Parodi | |
| 5,693,087 A | 12/1997 | Parodi | |
| 5,713,953 A | 2/1998 | Vallana | |
| 5,716,370 A | 2/1998 | Williamson, IV | |
| 5,735,859 A | 4/1998 | Fischell | |
| 5,741,326 A | 4/1998 | Solovay | |
| 5,741,333 A | 4/1998 | Frid | |
| 5,800,506 A | 9/1998 | Perouse | |
| 5,824,061 A | 10/1998 | Quijano | |
| 5,879,320 A | 3/1999 | Cazenave | |
| 5,895,419 A | 4/1999 | Tweden | |
| 5,910,170 A | 6/1999 | Reimink | |
| 6,010,531 A | 1/2000 | Donlon | |
| 6,042,607 A | 3/2000 | Williamson, IV | |
| 6,139,575 A | 10/2000 | Shu | |
| 6,287,334 B1 | 9/2001 | Moll | |
| 6,299,637 B1 | 10/2001 | Shaolian et al. | |
| 6,312,447 B1 | 11/2001 | Grimes | |
| 6,355,030 B1 | 3/2002 | Aldrich | |
| 6,402,780 B2 | 6/2002 | Williamson, IV | |
| 6,419,696 B1 | 7/2002 | Ortiz | |
| 6,425,916 B1 | 7/2002 | Garrison | |
| 6,440,164 B1 | 8/2002 | DiMatteo | |
| 6,451,054 B1 * | 9/2002 | Stevens | 623/2.11 |
| 6,454,799 B1 | 9/2002 | Schreck | |
| 6,461,366 B1 | 10/2002 | Seguin | |
| 6,503,272 B2 | 1/2003 | Duerig | |
| 6,508,833 B2 | 1/2003 | Pavcnik | |
| 6,530,952 B2 * | 3/2003 | Vesely | 623/2.18 |
| 6,564,805 B2 | 5/2003 | Garrison | |
| 6,569,196 B1 | 5/2003 | Vesely | |
| 6,602,286 B1 | 8/2003 | Strecker | |
| 6,629,534 B1 | 10/2003 | St. Goar | |
| 6,635,085 B1 | 10/2003 | Caffey | |
| 6,666,885 B2 | 12/2003 | Moe | |
| 6,666,886 B1 | 12/2003 | Tranquillo | |
| 6,669,725 B2 | 12/2003 | Scott | |
| 6,673,109 B2 | 1/2004 | Cox | |
| 6,676,698 B2 | 1/2004 | McGuckin, Jr. | |
| 6,676,702 B2 | 1/2004 | Mathis | |
| 6,682,558 B2 | 1/2004 | Tu | |
| 6,682,559 B2 | 1/2004 | Myers | |
| 6,685,739 B2 | 2/2004 | DiMatteo | |
| 6,692,512 B2 | 2/2004 | Jang | |
| 6,695,866 B1 | 2/2004 | Kuehn | |
| 6,695,878 B2 | 2/2004 | McGuckin | |
| 6,709,456 B2 | 3/2004 | Langberg | |
| 6,709,457 B1 | 3/2004 | Otte | |
| 6,716,241 B2 | 4/2004 | Wilder | |
| 6,716,244 B2 | 4/2004 | Klaco | |
| 6,719,767 B1 | 4/2004 | Kimblad | |
| 6,719,784 B2 | 4/2004 | Henderson | |
| 6,719,786 B2 | 4/2004 | Ryan | |
| 6,719,787 B2 | 4/2004 | Cox | |
| 6,719,788 B2 | 4/2004 | Cox | |
| 6,719,789 B2 | 4/2004 | Cox | |
| 6,719,790 B2 | 4/2004 | Brendzel | |
| 6,723,038 B1 | 4/2004 | Schroeder | |
| 6,723,122 B2 | 4/2004 | Yang | |
| 6,723,123 B1 | 4/2004 | Kazatchkov | |
| 6,726,715 B2 | 4/2004 | Sutherland | |
| 6,726,716 B2 | 4/2004 | Marquez | |
| 6,726,717 B2 | 4/2004 | Alfieri | |
| 6,730,118 B2 | 5/2004 | Spenser | |
| 6,730,121 B2 | 5/2004 | Ortiz | |
| 6,730,122 B1 | 5/2004 | Pan | |
| 6,736,845 B2 | 5/2004 | Marquez | |
| 6,736,846 B2 | 5/2004 | Cox | |
| 6,749,630 B2 | 6/2004 | McCarthy | |
| 6,752,813 B2 | 6/2004 | Goldfarb | |
| 6,752,828 B2 | 6/2004 | Thornton | |
| 6,755,857 B2 | 6/2004 | Peterson | |
| 6,761,734 B2 | 7/2004 | Suhr | |
| 6,761,735 B2 | 7/2004 | Eberhardt | |
| 6,764,494 B2 | 7/2004 | Menz | |
| 6,764,508 B1 | 7/2004 | Roehe | |
| 6,764,509 B2 | 7/2004 | Chinn | |
| 6,764,510 B2 | 7/2004 | Vidlund | |
| 6,767,362 B2 | 7/2004 | Schreck | |
| 6,769,434 B2 | 8/2004 | Liddicoat | |
| 6,770,083 B2 | 8/2004 | Seguin | |
| 6,780,200 B2 | 8/2004 | Jansen | |
| 6,786,924 B2 | 9/2004 | Ryan | |
| 6,786,925 B1 | 9/2004 | Schoon | |
| 6,790,229 B1 | 9/2004 | Berreklouw | |
| 6,790,230 B2 | 9/2004 | Beyersdorf | |
| 6,790,231 B2 | 9/2004 | Liddicoat | |
| 6,793,673 B2 | 9/2004 | Kowalsky | |
| 6,797,000 B2 | 9/2004 | Simpson | |
| 6,797,001 B2 | 9/2004 | Mathis | |
| 6,797,002 B2 | 9/2004 | Spence | |
| 6,802,860 B2 | 10/2004 | Cosgrove | |
| 6,805,710 B2 | 10/2004 | Bolling | |
| 6,805,711 B2 | 10/2004 | Quijano | |
| 6,810,882 B2 | 11/2004 | Langberg | |
| 6,821,297 B2 | 11/2004 | Snyders | |
| 6,824,562 B2 | 11/2004 | Mathis | |
| 6,830,584 B1 | 12/2004 | Seguin | |
| 6,830,585 B1 | 12/2004 | Artof | |
| 6,837,902 B2 | 1/2005 | Nguyen | |
| 6,840,246 B2 | 1/2005 | Downing | |
| 6,840,957 B2 | 1/2005 | DiMatteo | |
| 6,846,324 B2 | 1/2005 | Stobie | |
| 6,846,325 B2 | 1/2005 | Liddicoat | |
| 6,858,039 B2 | 2/2005 | McCarthy | |
| 6,869,444 B2 | 3/2005 | Gabbay | |
| 6,872,226 B2 | 3/2005 | Cali | |
| 6,875,224 B2 | 4/2005 | Grimes | |
| 6,875,230 B1 | 4/2005 | Morita | |
| 6,875,231 B2 | 4/2005 | Anduiza | |
| 6,881,199 B2 | 4/2005 | Wilk | |
| 6,881,224 B2 | 4/2005 | Kruse | |
| 6,883,522 B2 | 4/2005 | Spence | |
| 6,890,352 B1 | 5/2005 | Lentell | |
| 6,890,353 B2 | 5/2005 | Cohn | |
| 6,893,459 B1 | 5/2005 | Macoviak | |
| 6,893,460 B2 | 5/2005 | Spenser | |
| 6,896,700 B2 | 5/2005 | Lu | |
| 6,902,576 B2 | 6/2005 | Drasler | |
| 6,908,478 B2 | 6/2005 | Alferness | |
| 6,908,481 B2 | 6/2005 | Cribier | |
| 6,911,043 B2 | 6/2005 | Myers | |
| 6,913,608 B2 | 7/2005 | Liddicoat | |
| 6,916,338 B2 | 7/2005 | Speziali | |
| 6,918,917 B1 | 7/2005 | Nguyen | |
| 6,921,407 B2 | 7/2005 | Nguyen | |
| 6,921,811 B2 | 7/2005 | Zamora | |
| 6,926,715 B1 | 8/2005 | Hauck | |
| 6,926,730 B1 | 8/2005 | Nguyen | |
| 6,929,653 B2 | 8/2005 | Strecter | |
| 6,932,838 B2 | 8/2005 | Schwartz | |
| 6,936,067 B2 | 8/2005 | Buchanan | |
| 6,939,359 B2 | 9/2005 | Tu | |
| 6,942,694 B2 | 9/2005 | Liddicoat | |
| 6,945,957 B2 | 9/2005 | Freyman | |
| 6,945,978 B1 | 9/2005 | Hyde | |
| 6,945,996 B2 | 9/2005 | Sedransk | |
| 6,945,997 B2 | 9/2005 | Huynh | |
| 6,949,122 B2 | 9/2005 | Adams | |
| 6,951,571 B1 | 10/2005 | Srivastava | |
| 6,951,573 B1 | 10/2005 | Dilling | |
| 6,955,689 B2 | 10/2005 | Ryan | |
| 6,958,076 B2 | 10/2005 | Acosta | |
| 6,962,605 B2 | 11/2005 | Cosgrove | |
| 6,964,682 B2 | 11/2005 | Nguyen-Thien-Nhon | |
| 6,964,683 B2 | 11/2005 | Kowalsky | |
| 6,964,684 B2 | 11/2005 | Ortiz | |
| 6,966,925 B2 | 11/2005 | Stobie | |
| 6,966,926 B2 | 11/2005 | Mathis | |
| 6,974,464 B2 | 12/2005 | Quijano | |
| 6,974,474 B2 | 12/2005 | Pavcnik | |
| 6,974,476 B2 | 12/2005 | McGuckin, Jr. | |
| 6,976,995 B2 | 12/2005 | Mathis | |

| | | |
|---|---|---|
| 6,979,350 B2 | 12/2005 | Moll |
| 6,986,775 B2 | 1/2006 | Morales |
| 6,989,027 B2 | 1/2006 | Allen |
| 6,989,028 B2 | 1/2006 | Lashinski |
| 6,997,950 B2 | 2/2006 | Chawla |
| 6,997,951 B2 | 2/2006 | Solem |
| 7,004,176 B2 | 2/2006 | Lau |
| 7,007,396 B2 | 3/2006 | Rudko |
| 7,011,669 B2 | 3/2006 | Kimblad |
| 7,011,681 B2 | 3/2006 | Vesely |
| 7,011,682 B2 | 3/2006 | Lashinski |
| 7,018,406 B2 | 3/2006 | Seguin |
| 7,018,407 B1 | 3/2006 | Wright |
| 7,018,408 B2 | 3/2006 | Bailey |
| 7,022,134 B1 | 4/2006 | Quijano |
| 7,025,780 B2 | 4/2006 | Gabbay |
| 7,033,390 B2 | 4/2006 | Johnson |
| 7,037,333 B2 | 5/2006 | Myers |
| 7,037,334 B1 | 5/2006 | Hlavka |
| 7,041,128 B2 | 5/2006 | Mcguckin |
| 7,041,132 B2 | 5/2006 | Quijano |
| 7,044,966 B2 | 5/2006 | Svanidze |
| 7,044,967 B1 | 5/2006 | Solem |
| 7,048,754 B2 | 5/2006 | Martin |
| 7,048,757 B2 | 5/2006 | Shaknovich |
| 7,052,487 B2 | 5/2006 | Cohn |
| 7,052,507 B2 | 5/2006 | Wakuda |
| 7,063,722 B2 | 6/2006 | Marquez |
| 7,066,954 B2 | 6/2006 | Ryan |
| 7,070,616 B2 | 7/2006 | Majercak |
| 7,077,862 B2 | 7/2006 | Vidlund |
| 7,081,131 B2 | 7/2006 | Thornton |
| 7,087,064 B1 | 8/2006 | Hyde |
| 7,089,051 B2 | 8/2006 | Javerud |
| 7,090,695 B2 | 8/2006 | Solem |
| 7,569,071 B2 | 8/2009 | Haverkost |
| 7,951,189 B2 | 5/2011 | Haverkost |
| 2002/0013571 A1 | 1/2002 | Goldfarb |
| 2002/0026216 A1 | 2/2002 | Grimes |
| 2002/0082630 A1 | 6/2002 | Menz |
| 2002/0123802 A1 | 9/2002 | Snyders |
| 2002/0151970 A1 | 10/2002 | Garrison |
| 2002/0183835 A1 | 12/2002 | Taylor |
| 2002/0183838 A1 | 12/2002 | Liddicoat |
| 2002/0198594 A1 | 12/2002 | Schreck |
| 2003/0014104 A1* | 1/2003 | Cribier ................. 623/2.11 |
| 2003/0050694 A1 | 3/2003 | Yang |
| 2003/0130729 A1 | 7/2003 | Paniagua |
| 2003/0163194 A1 | 8/2003 | Quijano |
| 2003/0167071 A1 | 9/2003 | Martin |
| 2003/0171806 A1 | 9/2003 | Mathis |
| 2003/0199975 A1 | 10/2003 | Gabbay |
| 2003/0229394 A1 | 12/2003 | Ogle |
| 2003/0229395 A1 | 12/2003 | Cox |
| 2003/0233142 A1 | 12/2003 | Morales |
| 2003/0236568 A1 | 12/2003 | Hojeibane |
| 2003/0236569 A1 | 12/2003 | Mathis |
| 2004/0002719 A1 | 1/2004 | Oz |
| 2004/0003819 A1 | 1/2004 | St. Goar |
| 2004/0010305 A1 | 1/2004 | Alferness |
| 2004/0015230 A1 | 1/2004 | Moll |
| 2004/0015232 A1 | 1/2004 | Shu |
| 2004/0015233 A1 | 1/2004 | Jansen |
| 2004/0019374 A1 | 1/2004 | Hojeibane |
| 2004/0019377 A1 | 1/2004 | Taylor |
| 2004/0019378 A1 | 1/2004 | Hlavka |
| 2004/0024447 A1 | 2/2004 | Haverich |
| 2004/0024451 A1 | 2/2004 | Johnson |
| 2004/0024452 A1 | 2/2004 | Kruse |
| 2004/0030321 A1 | 2/2004 | Fangrow |
| 2004/0030381 A1 | 2/2004 | Shu |
| 2004/0030382 A1 | 2/2004 | St. Goar |
| 2004/0030405 A1 | 2/2004 | Carpentier |
| 2004/0034380 A1 | 2/2004 | Woolfson |
| 2004/0034411 A1 | 2/2004 | Quijano |
| 2004/0039436 A1 | 2/2004 | Spenser |
| 2004/0039442 A1 | 2/2004 | St. Goar |
| 2004/0039443 A1 | 2/2004 | Solem |
| 2004/0044350 A1 | 3/2004 | Martin |
| 2004/0044365 A1 | 3/2004 | Bachman |
| 2004/0044403 A1 | 3/2004 | Bischoff |
| 2004/0049207 A1 | 3/2004 | Goldfarb |
| 2004/0049211 A1 | 3/2004 | Tremulis |
| 2004/0049266 A1 | 3/2004 | Anduiza |
| 2004/0059351 A1 | 3/2004 | Eigler |
| 2004/0059411 A1 | 3/2004 | Strecker |
| 2004/0059412 A1 | 3/2004 | Lytle |
| 2004/0060161 A1 | 4/2004 | Leal |
| 2004/0073301 A1 | 4/2004 | Donlon |
| 2004/0073302 A1 | 4/2004 | Rourke |
| 2004/0078072 A1 | 4/2004 | Tu |
| 2004/0078074 A1 | 4/2004 | Anderson |
| 2004/0082910 A1 | 4/2004 | Constantz |
| 2004/0082923 A1 | 4/2004 | Field |
| 2004/0082991 A1 | 4/2004 | Nguyen |
| 2004/0087975 A1 | 5/2004 | Lucatero |
| 2004/0088045 A1 | 5/2004 | Cox |
| 2004/0088046 A1 | 5/2004 | Speziali |
| 2004/0092858 A1 | 5/2004 | Wilson |
| 2004/0093060 A1 | 5/2004 | Seguin |
| 2004/0093070 A1 | 5/2004 | Hojeibane |
| 2004/0093080 A1 | 5/2004 | Helmus |
| 2004/0097979 A1 | 5/2004 | Svanidze |
| 2004/0098098 A1 | 5/2004 | McGuckin, Jr. |
| 2004/0098112 A1 | 5/2004 | Dimatteo |
| 2004/0102839 A1 | 5/2004 | Cohn |
| 2004/0102840 A1 | 5/2004 | Solem |
| 2004/0102842 A1 | 5/2004 | Jansen |
| 2004/0106976 A1 | 6/2004 | Bailey |
| 2004/0106990 A1 | 6/2004 | Spence |
| 2004/0106991 A1 | 6/2004 | Hopkins |
| 2004/0111096 A1 | 6/2004 | Tu |
| 2004/0117009 A1 | 6/2004 | Cali |
| 2004/0122448 A1 | 6/2004 | Levine |
| 2004/0122512 A1 | 6/2004 | Navia |
| 2004/0122513 A1 | 6/2004 | Navia |
| 2004/0122514 A1 | 6/2004 | Fogarty |
| 2004/0122515 A1 | 6/2004 | Chu |
| 2004/0122516 A1 | 6/2004 | Fogarty |
| 2004/0127979 A1 | 7/2004 | Wilson |
| 2004/0127980 A1 | 7/2004 | Kowalsky |
| 2004/0127981 A1 | 7/2004 | Rahdert |
| 2004/0127982 A1 | 7/2004 | Machold |
| 2004/0133220 A1 | 7/2004 | Lashinski |
| 2004/0133267 A1 | 7/2004 | Lane |
| 2004/0133273 A1 | 7/2004 | Cox |
| 2004/0138742 A1 | 7/2004 | Myers |
| 2004/0138743 A1 | 7/2004 | Myers |
| 2004/0138744 A1 | 7/2004 | Lashinski |
| 2004/0138745 A1 | 7/2004 | Macoviak |
| 2004/0148018 A1 | 7/2004 | Carpentier |
| 2004/0148019 A1 | 7/2004 | Vidlund |
| 2004/0148020 A1 | 7/2004 | Vidlund |
| 2004/0153052 A1 | 8/2004 | Mathis |
| 2004/0153146 A1 | 8/2004 | Lashinski |
| 2004/0153147 A1 | 8/2004 | Mathis |
| 2004/0158321 A1 | 8/2004 | Reuter |
| 2004/0162610 A1 | 8/2004 | Liska |
| 2004/0167539 A1 | 8/2004 | Kuehn |
| 2004/0167620 A1 | 8/2004 | Ortiz |
| 2004/0172046 A1 | 9/2004 | Hlavka |
| 2004/0176839 A1 | 9/2004 | Huynh |
| 2004/0176840 A1 | 9/2004 | Langberg |
| 2004/0181238 A1 | 9/2004 | Zarbatany |
| 2004/0186444 A1 | 9/2004 | Daly |
| 2004/0186558 A1 | 9/2004 | Pavcnik |
| 2004/0186561 A1 | 9/2004 | Mcguckin |
| 2004/0186563 A1 | 9/2004 | Lobbi |
| 2004/0186565 A1 | 9/2004 | Schreck |
| 2004/0186566 A1 | 9/2004 | Hindrichs |
| 2004/0193191 A1 | 9/2004 | Starksen |
| 2004/0193253 A1 | 9/2004 | Thorpe |
| 2004/0193260 A1 | 9/2004 | Alferness |
| 2004/0199155 A1 | 10/2004 | Mollenauer |
| 2004/0199183 A1 | 10/2004 | Oz |
| 2004/0199191 A1 | 10/2004 | Schwartz |
| 2004/0204758 A1 | 10/2004 | Eberhardt |
| 2004/0206363 A1 | 10/2004 | Mccarthy |

| | | | | | | |
|---|---|---|---|---|---|---|
| 2004/0210240 A1 | 10/2004 | Saint | | 2005/0075718 A1 | 4/2005 | Nguyen |
| 2004/0210301 A1 | 10/2004 | Obermiller | | 2005/0075719 A1 | 4/2005 | Bergheim |
| 2004/0210303 A1 | 10/2004 | Sedransk | | 2005/0075720 A1 | 4/2005 | Nguyen |
| 2004/0210304 A1 | 10/2004 | Seguin | | 2005/0075723 A1 | 4/2005 | Schroeder |
| 2004/0210305 A1 | 10/2004 | Shu | | 2005/0075724 A1 | 4/2005 | Svanidze |
| 2004/0210306 A1 | 10/2004 | Quijano | | 2005/0075725 A1 | 4/2005 | Rowe |
| 2004/0210307 A1 | 10/2004 | Khairkhahan | | 2005/0075726 A1 | 4/2005 | Svanidze |
| 2004/0215333 A1 | 10/2004 | Duran | | 2005/0075729 A1 | 4/2005 | Nguyen |
| 2004/0215339 A1 | 10/2004 | Drasler | | 2005/0075730 A1 | 4/2005 | Myers |
| 2004/0220654 A1 | 11/2004 | Mathis | | 2005/0075731 A1 | 4/2005 | Artof |
| 2004/0220657 A1 | 11/2004 | Nieminen | | 2005/0080483 A1 | 4/2005 | Solem |
| 2004/0225322 A1 | 11/2004 | Garrison | | 2005/0085900 A1 | 4/2005 | Case |
| 2004/0225344 A1 | 11/2004 | Hoffa | | 2005/0085903 A1 | 4/2005 | Lau |
| 2004/0225348 A1 | 11/2004 | Case | | 2005/0085904 A1 | 4/2005 | Lemmon |
| 2004/0225352 A1 | 11/2004 | Osborne | | 2005/0090846 A1 | 4/2005 | Pedersen |
| 2004/0225353 A1 | 11/2004 | McGuckin, Jr. | | 2005/0096735 A1 | 5/2005 | Hojeibane |
| 2004/0225354 A1 | 11/2004 | Allen | | 2005/0096738 A1 | 5/2005 | Cali |
| 2004/0225355 A1 | 11/2004 | Stevens | | 2005/0096739 A1 | 5/2005 | Cao |
| 2004/0225356 A1 | 11/2004 | Frater | | 2005/0096740 A1 | 5/2005 | Langberg |
| 2004/0230117 A1 | 11/2004 | Tosaya | | 2005/0101975 A1 | 5/2005 | Nguyen |
| 2004/0230297 A1 | 11/2004 | Thornton | | 2005/0102026 A1 | 5/2005 | Turner |
| 2004/0236411 A1 | 11/2004 | Sarac | | 2005/0107810 A1 | 5/2005 | Morales |
| 2004/0236418 A1 | 11/2004 | Stevens | | 2005/0107811 A1 | 5/2005 | Starksen |
| 2004/0236419 A1 | 11/2004 | Milo | | 2005/0107812 A1 | 5/2005 | Starksen |
| 2004/0243153 A1 | 12/2004 | Liddicoat | | 2005/0107872 A1 | 5/2005 | Mensah |
| 2004/0243219 A1 | 12/2004 | Fischer | | 2005/0113910 A1 | 5/2005 | Paniagua |
| 2004/0243227 A1 | 12/2004 | Starksen | | 2005/0119673 A1 | 6/2005 | Gordon |
| 2004/0243228 A1 | 12/2004 | Kowalsky | | 2005/0119734 A1 | 6/2005 | Spence |
| 2004/0243230 A1 | 12/2004 | Navia | | 2005/0119735 A1 | 6/2005 | Spence |
| 2004/0254600 A1 | 12/2004 | Zarbatany | | 2005/0125011 A1 | 6/2005 | Spence |
| 2004/0254636 A1 | 12/2004 | Flagle | | 2005/0131438 A1 | 6/2005 | Cohn |
| 2004/0260276 A1 | 12/2004 | Rudko | | 2005/0137449 A1 | 6/2005 | Nieminen |
| 2004/0260317 A1 | 12/2004 | Bloom | | 2005/0137450 A1 | 6/2005 | Aronson |
| 2004/0260322 A1 | 12/2004 | Rudko | | 2005/0137451 A1 | 6/2005 | Gordon |
| 2004/0260389 A1 | 12/2004 | Case | | 2005/0137676 A1 | 6/2005 | Richardson |
| 2004/0260390 A1 | 12/2004 | Sarac | | 2005/0137681 A1 | 6/2005 | Shoemaker |
| 2004/0260393 A1 | 12/2004 | Rahdert | | 2005/0137682 A1 | 6/2005 | Justin |
| 2004/0260394 A1 | 12/2004 | Douk | | 2005/0137685 A1 | 6/2005 | Nieminen |
| 2004/0267357 A1 | 12/2004 | Allen | | 2005/0137686 A1 | 6/2005 | Salahieh |
| 2005/0004583 A1 | 1/2005 | Oz | | 2005/0137688 A1 | 6/2005 | Salahieh |
| 2005/0004667 A1 | 1/2005 | Swinford | | 2005/0137689 A1 | 6/2005 | Salahieh |
| 2005/0010285 A1 | 1/2005 | Lambrecht | | 2005/0137690 A1 | 6/2005 | Salahieh |
| 2005/0010287 A1 | 1/2005 | Macoviak | | 2005/0137691 A1 | 6/2005 | Salahieh |
| 2005/0015112 A1 | 1/2005 | Cohn | | 2005/0137692 A1 | 6/2005 | Haug |
| 2005/0021056 A1 | 1/2005 | St. Goar | | 2005/0137693 A1 | 6/2005 | Haug |
| 2005/0021136 A1 | 1/2005 | Xie | | 2005/0137694 A1 | 6/2005 | Haug |
| 2005/0027261 A1 | 2/2005 | Weaver | | 2005/0137696 A1 | 6/2005 | Salahieh |
| 2005/0027348 A1 | 2/2005 | Case | | 2005/0137697 A1 | 6/2005 | Salahieh |
| 2005/0027351 A1 | 2/2005 | Reuter | | 2005/0137698 A1 | 6/2005 | Salahieh |
| 2005/0027353 A1 | 2/2005 | Alferness | | 2005/0137699 A1 | 6/2005 | Salahieh |
| 2005/0033398 A1 | 2/2005 | Seguin | | 2005/0137700 A1 | 6/2005 | Spence |
| 2005/0033419 A1 | 2/2005 | Alferness | | 2005/0137701 A1 | 6/2005 | Salahieh |
| 2005/0033446 A1 | 2/2005 | Deem | | 2005/0137702 A1 | 6/2005 | Haug |
| 2005/0038506 A1 | 2/2005 | Webler | | 2005/0143807 A1 | 6/2005 | Pavcnik |
| 2005/0038507 A1 | 2/2005 | Alferness | | 2005/0143809 A1 | 6/2005 | Salahieh |
| 2005/0043790 A1 | 2/2005 | Seguin | | 2005/0143810 A1 | 6/2005 | Dauner |
| 2005/0043792 A1 | 2/2005 | Solem | | 2005/0143811 A1 | 6/2005 | Realyvasquez |
| 2005/0049679 A1 | 3/2005 | Taylor | | 2005/0149014 A1 | 7/2005 | Hauck |
| 2005/0049692 A1 | 3/2005 | Numamoto | | 2005/0149179 A1 | 7/2005 | Mathis |
| 2005/0049696 A1 | 3/2005 | Siess | | 2005/0149180 A1 | 7/2005 | Mathis |
| 2005/0049697 A1 | 3/2005 | Sievers | | 2005/0149181 A1 | 7/2005 | Eberhardt |
| 2005/0054977 A1 | 3/2005 | Laird | | 2005/0159810 A1 | 7/2005 | Filsoufi |
| 2005/0055079 A1 | 3/2005 | Duran | | 2005/0159811 A1 | 7/2005 | Lane |
| 2005/0055087 A1 | 3/2005 | Starksen | | 2005/0165477 A1 | 7/2005 | Anduiza |
| 2005/0055088 A1 | 3/2005 | Liddicoat | | 2005/0165478 A1 | 7/2005 | Song |
| 2005/0055089 A1 | 3/2005 | Macoviak | | 2005/0171472 A1 | 8/2005 | Lutter |
| 2005/0060029 A1 | 3/2005 | Le | | 2005/0171601 A1 | 8/2005 | Cosgrove |
| 2005/0060030 A1 | 3/2005 | Lashinski | | 2005/0177227 A1 | 8/2005 | Heim |
| 2005/0065460 A1 | 3/2005 | Laird | | 2005/0177228 A1 | 8/2005 | Solem |
| 2005/0065550 A1 | 3/2005 | Starksen | | 2005/0182483 A1 | 8/2005 | Osborne |
| 2005/0065594 A1 | 3/2005 | Dimatteo | | 2005/0184122 A1 | 8/2005 | Hlavka |
| 2005/0065597 A1 | 3/2005 | Lansac | | 2005/0187614 A1 | 8/2005 | Agnew |
| 2005/0070998 A1 | 3/2005 | Rourke | | 2005/0187616 A1 | 8/2005 | Realyvasquez |
| 2005/0075584 A1 | 4/2005 | Cali | | 2005/0187617 A1 | 8/2005 | Navia |
| 2005/0075659 A1 | 4/2005 | Realyvasquez | | 2005/0192606 A1 | 9/2005 | Paul |
| 2005/0075662 A1 | 4/2005 | Pedersen | | 2005/0192665 A1 | 9/2005 | Spenser |
| 2005/0075712 A1 | 4/2005 | Biancucci | | 2005/0197692 A1 | 9/2005 | Pai |
| 2005/0075713 A1 | 4/2005 | Biancucci | | 2005/0197693 A1 | 9/2005 | Pai |
| 2005/0075717 A1 | 4/2005 | Nguyen | | 2005/0197694 A1 | 9/2005 | Pai |

| | | |
|---|---|---|
| 2005/0203549 A1 | 9/2005 | Realyvasquez |
| 2005/0203605 A1 | 9/2005 | Dolan |
| 2005/0203614 A1 | 9/2005 | Forster |
| 2005/0203615 A1 | 9/2005 | Forster |
| 2005/0203616 A1 | 9/2005 | Cribier |
| 2005/0203617 A1 | 9/2005 | Forster |
| 2005/0203618 A1 | 9/2005 | Sharkawy |
| 2005/0216039 A1 | 9/2005 | Lederman |
| 2005/0216077 A1 | 9/2005 | Mathis |
| 2005/0216078 A1 | 9/2005 | Starksen |
| 2005/0222675 A1 | 10/2005 | Sauter |
| 2005/0222678 A1 | 10/2005 | Lashinski |
| 2005/0228422 A1 | 10/2005 | Machold |
| 2005/0228479 A1 | 10/2005 | Pavcnik |
| 2005/0228486 A1 | 10/2005 | Case |
| 2005/0228494 A1 | 10/2005 | Marquez |
| 2005/0228495 A1 | 10/2005 | Macoviak |
| 2005/0228496 A1 | 10/2005 | Mensah |
| 2005/0234541 A1 | 10/2005 | Hunt |
| 2005/0234546 A1 | 10/2005 | Nugent |
| 2005/0240200 A1 | 10/2005 | Bergheim |
| 2005/0240202 A1 | 10/2005 | Shennib |
| 2005/0240255 A1 | 10/2005 | Schaeffer |
| 2005/0240259 A1 | 10/2005 | Sisken |
| 2005/0240262 A1 | 10/2005 | White |
| 2005/0244460 A1 | 11/2005 | Alferiev |
| 2005/0246013 A1 | 11/2005 | Gabbay |
| 2005/0251251 A1 | 11/2005 | Cribier |
| 2005/0256566 A1 | 11/2005 | Gabbay |
| 2005/0261704 A1 | 11/2005 | Mathis |
| 2005/0261759 A1 | 11/2005 | Lambrecht |
| 2005/0267493 A1 | 12/2005 | Schreck |
| 2005/0267560 A1 | 12/2005 | Bates |
| 2005/0267565 A1 | 12/2005 | Dave |
| 2005/0267571 A1 | 12/2005 | Spence |
| 2005/0267573 A9 | 12/2005 | Macoviak |
| 2005/0267574 A1 | 12/2005 | Cohn |
| 2005/0272969 A1 | 12/2005 | Alferness |
| 2005/0273160 A1 | 12/2005 | Lashinski |
| 2005/0278015 A1 | 12/2005 | Dave |
| 2005/0283178 A1 | 12/2005 | Flagle |
| 2005/0283231 A1 | 12/2005 | Haug |
| 2005/0288779 A1 | 12/2005 | Shaoulian |
| 2006/0000715 A1 | 1/2006 | Whitcher |
| 2006/0004439 A1 | 1/2006 | Spenser |
| 2006/0004442 A1 | 1/2006 | Spenser |
| 2006/0009841 A1 | 1/2006 | Mcguckin |
| 2006/0009842 A1 | 1/2006 | Huynh |
| 2006/0013805 A1 | 1/2006 | Hebbel |
| 2006/0013855 A1 | 1/2006 | Carpenter |
| 2006/0015136 A1 | 1/2006 | Besselink |
| 2006/0015178 A1 | 1/2006 | Moaddeb |
| 2006/0015179 A1 | 1/2006 | Bulman-Fleming |
| 2006/0020275 A1 | 1/2006 | Goldfarb |
| 2006/0020327 A1 | 1/2006 | Lashinski |
| 2006/0020332 A1 | 1/2006 | Lashinski |
| 2006/0020334 A1 | 1/2006 | Lashinski |
| 2006/0020335 A1 | 1/2006 | Kowalsky |
| 2006/0020336 A1 | 1/2006 | Liddicoat |
| 2006/0025750 A1 | 2/2006 | Starksen |
| 2006/0025784 A1 | 2/2006 | Starksen |
| 2006/0025787 A1 | 2/2006 | Morales |
| 2006/0025854 A1 | 2/2006 | Lashinski |
| 2006/0025855 A1 | 2/2006 | Lashinski |
| 2006/0025856 A1 | 2/2006 | Ryan |
| 2006/0025857 A1 | 2/2006 | Bergheim |
| 2006/0030747 A1 | 2/2006 | Kantrowitz |
| 2006/0030866 A1 | 2/2006 | Schreck |
| 2006/0030882 A1 | 2/2006 | Adams |
| 2006/0030885 A1 | 2/2006 | Hyde |
| 2006/0036317 A1 | 2/2006 | Vidlund |
| 2006/0041305 A1 | 2/2006 | Lauterjung |
| 2006/0041306 A1 | 2/2006 | Vidlund |
| 2006/0047297 A1 | 3/2006 | Case |
| 2006/0047338 A1 | 3/2006 | Jenson |
| 2006/0047343 A1 | 3/2006 | Oviatt |
| 2006/0052804 A1 | 3/2006 | Mialhe |
| 2006/0052867 A1 | 3/2006 | Revuelta |
| 2006/0058817 A1 | 3/2006 | Starksen |
| 2006/0058865 A1 | 3/2006 | Case |
| 2006/0058871 A1 | 3/2006 | Zakay |
| 2006/0058889 A1 | 3/2006 | Case |
| 2006/0064115 A1 | 3/2006 | Allen |
| 2006/0064116 A1 | 3/2006 | Allen |
| 2006/0064118 A1 | 3/2006 | Kimblad |
| 2006/0064174 A1 | 3/2006 | Zadno |
| 2006/0069400 A1 | 3/2006 | Burnett |
| 2006/0069430 A9 | 3/2006 | Rahdert |
| 2006/0074483 A1 | 4/2006 | Schrayer |
| 2006/0074484 A1 | 4/2006 | Huber |
| 2006/0074485 A1 | 4/2006 | Realyvasquez |
| 2006/0085060 A1 | 4/2006 | Campbell |
| 2006/0089708 A1 | 4/2006 | Osse |
| 2006/0095115 A1 | 5/2006 | Bladillah |
| 2006/0095125 A1 | 5/2006 | Chinn |
| 2006/0099326 A1 | 5/2006 | Keogh |
| 2006/0100697 A1 | 5/2006 | Casanova |
| 2006/0100699 A1 | 5/2006 | Vidlund |
| 2006/0106278 A1 | 5/2006 | Machold |
| 2006/0106279 A1 | 5/2006 | Machold |
| 2006/0106456 A9 | 5/2006 | Machold |
| 2006/0111660 A1 | 5/2006 | Wolf |
| 2006/0111773 A1 | 5/2006 | Rittgers |
| 2006/0111774 A1 | 5/2006 | Samkov |
| 2006/0116572 A1 | 6/2006 | Case |
| 2006/0116756 A1 | 6/2006 | Solem |
| 2006/0122686 A1 | 6/2006 | Gilad |
| 2006/0122692 A1 | 6/2006 | Gilad |
| 2006/0122693 A1 | 6/2006 | Biadillah |
| 2006/0127443 A1 | 6/2006 | Helmus |
| 2006/0129235 A1 | 6/2006 | Seguin |
| 2006/0129236 A1 | 6/2006 | Mccarthy |
| 2006/0135476 A1 | 6/2006 | Kutryk |
| 2006/0135964 A1 | 6/2006 | Vesely |
| 2006/0135967 A1 | 6/2006 | Realyvasquez |
| 2006/0136044 A1 | 6/2006 | Osborne |
| 2006/0136045 A1 | 6/2006 | Flagle |
| 2006/0136052 A1 | 6/2006 | Vesely |
| 2006/0136054 A1 | 6/2006 | Berg |
| 2006/0142846 A1 | 6/2006 | Pavcnik |
| 2006/0142847 A1 | 6/2006 | Shaknovich |
| 2006/0142848 A1 | 6/2006 | Gabbay |
| 2006/0142854 A1 | 6/2006 | Alferness |
| 2006/0149358 A1 | 7/2006 | Zilla |
| 2006/0149360 A1 | 7/2006 | Schwammenthal |
| 2006/0149367 A1 | 7/2006 | Sieracki |
| 2006/0149368 A1 | 7/2006 | Spence |
| 2006/0161133 A1 | 7/2006 | Laird |
| 2006/0161248 A1 | 7/2006 | Case |
| 2006/0161250 A1 | 7/2006 | Shaw |
| 2006/0167468 A1 | 7/2006 | Gabbay |
| 2006/0167541 A1 | 7/2006 | Lattouf |
| 2006/0167542 A1 | 7/2006 | Quintessenza |
| 2006/0167543 A1 | 7/2006 | Bailey |
| 2006/0195180 A1* | 8/2006 | Kheradvar et al. .......... 623/2.11 |
| 2008/0319526 A1 | 12/2008 | Hill |
| 2011/0230949 A1 | 9/2011 | Haverkost |

FOREIGN PATENT DOCUMENTS

| | | |
|---|---|---|
| FR | 2728457 | 6/1996 |
| WO | 8800459 | 1/1988 |
| WO | 9015582 | 12/1990 |
| WO | 9501669 | 1/1995 |
| WO | 9619159 | 6/1996 |
| WO | 9803656 | 1/1998 |
| WO | 9846115 | 10/1998 |
| WO | 9904724 | 2/1999 |
| WO | 0047139 | 8/2000 |
| WO | 0067679 | 11/2000 |
| WO | 0115650 | 3/2001 |
| WO | 0117462 | 3/2001 |
| WO | 0154624 | 8/2001 |
| WO | 03047468 | 6/2003 |
| WO | 03084443 | 10/2003 |
| WO | 2004019825 | 3/2004 |
| WO | 2004021893 | 3/2004 |
| WO | 2004023980 | 3/2004 |
| WO | 2004030568 | 4/2004 |

| | | | | | | |
|---|---|---|---|---|---|---|
| WO | 2004030569 | 4/2004 | | WO | 2005027790 | 3/2005 |
| WO | 2004030570 | 4/2004 | | WO | 2005027797 | 3/2005 |
| WO | 2004032724 | 4/2004 | | WO | 2005034812 | 4/2005 |
| WO | 2004032796 | 4/2004 | | WO | 2005039428 | 5/2005 |
| WO | 2004037128 | 5/2004 | | WO | 2005039452 | 5/2005 |
| WO | 2004037317 | 5/2004 | | WO | 2005046488 | 5/2005 |
| WO | 2004039432 | 5/2004 | | WO | 2005046528 | 5/2005 |
| WO | 2004043265 | 5/2004 | | WO | 2005046529 | 5/2005 |
| WO | 2004043273 | 5/2004 | | WO | 2005046531 | 5/2005 |
| WO | 2004043293 | 5/2004 | | WO | 2005049103 | 6/2005 |
| WO | 2004045370 | 6/2004 | | WO | 2005051226 | 6/2005 |
| WO | 2004045378 | 6/2004 | | WO | 2005055811 | 6/2005 |
| WO | 2004045463 | 6/2004 | | WO | 2005055883 | 6/2005 |
| WO | 2004047677 | 6/2004 | | WO | 2005058206 | 6/2005 |
| WO | 2004060217 | 7/2004 | | WO | 2005065585 | 7/2005 |
| WO | 2004060470 | 7/2004 | | WO | 2005065593 | 7/2005 |
| WO | 2004062725 | 7/2004 | | WO | 2005065594 | 7/2005 |
| WO | 2004066803 | 8/2004 | | WO | 2005070342 | 8/2005 |
| WO | 2004066826 | 8/2004 | | WO | 2005070343 | 8/2005 |
| WO | 2004069287 | 8/2004 | | WO | 2005072654 | 8/2005 |
| WO | 2004075789 | 9/2004 | | WO | 2005072655 | 8/2005 |
| WO | 2004080352 | 9/2004 | | WO | 2005079706 | 9/2005 |
| WO | 2004082523 | 9/2004 | | WO | 2005082288 | 9/2005 |
| WO | 2004082527 | 9/2004 | | WO | 2005082289 | 9/2005 |
| WO | 2004082528 | 9/2004 | | WO | 2005084595 | 9/2005 |
| WO | 2004082536 | 9/2004 | | WO | 2005087139 | 9/2005 |
| WO | 2004082537 | 9/2004 | | WO | 2005087140 | 9/2005 |
| WO | 2004082538 | 9/2004 | | WO | 2006000763 | 1/2006 |
| WO | 2004082757 | 9/2004 | | WO | 2006000776 | 1/2006 |
| WO | 2004084746 | 10/2004 | | WO | 2006002492 | 1/2006 |
| WO | 2004084770 | 10/2004 | | WO | 2006004679 | 1/2006 |
| WO | 2004089246 | 10/2004 | | WO | 2006005015 | 1/2006 |
| WO | 2004089250 | 10/2004 | | WO | 2006009690 | 1/2006 |
| WO | 2004089253 | 10/2004 | | WO | 2006011127 | 2/2006 |
| WO | 2004091449 | 10/2004 | | WO | 2006012011 | 2/2006 |
| WO | 2004091454 | 10/2004 | | WO | 2006012013 | 2/2006 |
| WO | 2004093638 | 11/2004 | | WO | 2006012038 | 2/2006 |
| WO | 2004093726 | 11/2004 | | WO | 2006012068 | 2/2006 |
| WO | 2004093728 | 11/2004 | | WO | 2006012322 | 2/2006 |
| WO | 2004093730 | 11/2004 | | WO | 2006019498 | 2/2006 |
| WO | 2004093745 | 11/2004 | | WO | 2006026371 | 3/2006 |
| WO | 2004093935 | 11/2004 | | WO | 2006026377 | 3/2006 |
| WO | 2004096100 | 11/2004 | | WO | 2006026912 | 3/2006 |
| WO | 2004103222 | 12/2004 | | WO | 2006027499 | 3/2006 |
| WO | 2004103223 | 12/2004 | | WO | 2006028821 | 3/2006 |
| WO | 2004105584 | 12/2004 | | WO | 2006029062 | 3/2006 |
| WO | 2004105651 | 12/2004 | | WO | 2006031436 | 3/2006 |
| WO | 2004112582 | 12/2004 | | WO | 2006031469 | 3/2006 |
| WO | 2004112585 | 12/2004 | | WO | 2006032051 | 3/2006 |
| WO | 2004112643 | 12/2004 | | WO | 2006034245 | 3/2006 |
| WO | 2004112652 | 12/2004 | | WO | 2006035415 | 4/2006 |
| WO | 2004112657 | 12/2004 | | WO | 2006041505 | 4/2006 |
| WO | 2004112658 | 12/2004 | | WO | 2006044679 | 4/2006 |
| WO | 2005000152 | 1/2005 | | WO | 2006048664 | 5/2006 |
| WO | 2005002424 | 1/2005 | | WO | 2006050459 | 5/2006 |
| WO | 2005002466 | 1/2005 | | WO | 2006050460 | 5/2006 |
| WO | 2005004753 | 1/2005 | | WO | 2006054107 | 5/2006 |
| WO | 2005007017 | 1/2005 | | WO | 2006054930 | 5/2006 |
| WO | 2005007018 | 1/2005 | | WO | 2006055982 | 5/2006 |
| WO | 2005007036 | 1/2005 | | WO | 2006060546 | 6/2006 |
| WO | 2005007037 | 1/2005 | | WO | 2006063108 | 6/2006 |
| WO | 2005048883 | 1/2005 | | WO | 2006063181 | 6/2006 |
| WO | 2005009285 | 2/2005 | | WO | 2006063199 | 6/2006 |
| WO | 2005009286 | 2/2005 | | WO | 2006064490 | 6/2006 |
| WO | 2005009505 | 2/2005 | | WO | 2006065212 | 6/2006 |
| WO | 2005009506 | 2/2005 | | WO | 2006065930 | 6/2006 |
| WO | 2005011473 | 2/2005 | | WO | 2006066148 | 6/2006 |
| WO | 2005011534 | 2/2005 | | WO | 2006066150 | 6/2006 |
| WO | 2005011535 | 2/2005 | | WO | 2006069094 | 6/2006 |
| WO | 2005013860 | 2/2005 | | WO | 2006070372 | 7/2006 |
| WO | 2005018507 | 3/2005 | | WO | 2006073628 | 7/2006 |
| WO | 2005021063 | 3/2005 | | WO | 2006076890 | 7/2006 |
| WO | 2005023155 | 3/2005 | | | | |
| WO | 2005025644 | 3/2005 | | * cited by examiner | | |

PERCUTANEOUS VALVE, SYSTEM, AND METHOD

This application is a continuation of U.S. application Ser. No. 12/012,898, filed Feb. 5, 2008, which claims the benefit of U.S. Provisional Application Ser. No. 60/899,446, filed Feb. 5, 2007, the entire contents of which are incorporated herein by reference.

TECHNICAL FIELD

The present disclosure relates generally to apparatus', systems, and methods for use in the vascular system; and more particularly to a percutaneous valve, system, and method for use in the vasculature system.

BACKGROUND

Valves can become damaged and/or diseased for a variety of reasons. Damaged and/or diseased valves are grouped according to which valve or valves are involved, and the amount of blood flow that is disrupted by the damaged and/or diseased valve. For example, the most common cardiac valve diseases occur in the mitral and aortic valves. Diseases of the tricuspid and pulmonary valves are fairly rare.

The aortic valve regulates the blood flow from the heart's left ventricle into the aorta. The aorta is the main artery that supplies oxygenated blood to the body. As a result, diseases of the aortic valve can have a significant impact on an individual's health. Examples of such diseases include aortic regurgitation and aortic stenosis.

Aortic regurgitation is also called aortic insufficiency or aortic incompetence. It is a condition in which blood flows backward from a widened or weakened aortic valve into the left ventricle of the heart. In its most serious form, aortic regurgitation is caused by an infection that leaves holes in the valve leaflets. Symptoms of aortic regurgitation may not appear for years. When symptoms do appear, it is because the left ventricle must work harder relative to an uncompromised aortic valve to make up for the backflow of blood. The ventricle eventually gets larger and fluid backs up.

Aortic stenosis is a narrowing or blockage of the aortic valve. Aortic stenosis occurs when the valve leaflets of the aorta become coated with deposits. The deposits change the shape of the leaflets and reduce blood flow through the valve. Again, the left ventricle has to work harder relative to an uncompromised aortic valve to make up for the reduced blood flow. Over time, the extra work can weaken the heart muscle.

DETAILED DESCRIPTION

Figure 1A:
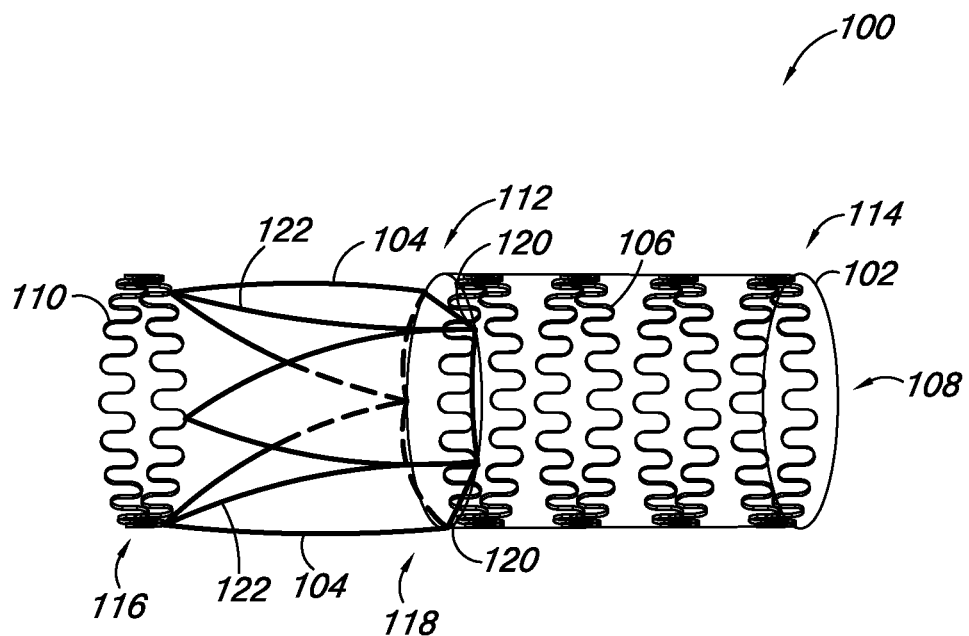
FIGS. 1A-1B provide an embodiment of a valve of the present disclosure.

Embodiments of the present disclosure are directed to an apparatus, system, and method for percutaneous valve replacement and/or augmentation. For example, the apparatus can include a valve that can be used to replace an incompetent valve (e.g., an aortic valve, a mitral valve, a tricuspid valve, or a pulmonary valve) or vein in a body lumen. Embodiments of the valve include a valve frame having frame members that define a lumen, and a valve leaflet coupled to the valve frame.

In the various embodiments, the valve leaflets extend away from the lumen of the valve. This configuration allows for more flexibility in the valve frame design as well as the valve leaflet design since the valve is not delivered to a treatment site with the valve leaflets inside the valve frame. In addition to more flexibility in design, this configuration allows for a lower profile of the delivered valve since the valve leaflets are outside the valve frame, allowing the valve frame to be compressed to a greater degree. For example, the valve frame can be at least partially balloon deployed without compressing, or sandwiching, the valve leaflets between the inflatable balloon and the valve frame. Once the valve frame is deployed, the valve leaflets and valve frame can be transitioned to within the lumen of the valve frame and the leaflet transition member can be expanded to secure the leaflet transition member and the valve leaflets into a position to function as a valve. Embodiments of the present disclosure can be used as a prosthetic cardiac valve and/or a prosthetic venous valve, as well as other valves.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments of valve and/or system. In addition, as will be appreciated the proportion and the relative scale of the elements provided in the figures are intended to illustrate the embodiments of the present invention, and should not be taken in a limiting sense.

Various embodiments of the present disclosure are illustrated in the figures. Generally, the valve can be implanted within the fluid passageway of a body lumen, for example, for replacement or augmentation of a valve structure within the body lumen (e.g., an aortic valve), to regulate the flow of a bodily fluid through the body lumen in a single direction.

Figure 1B:
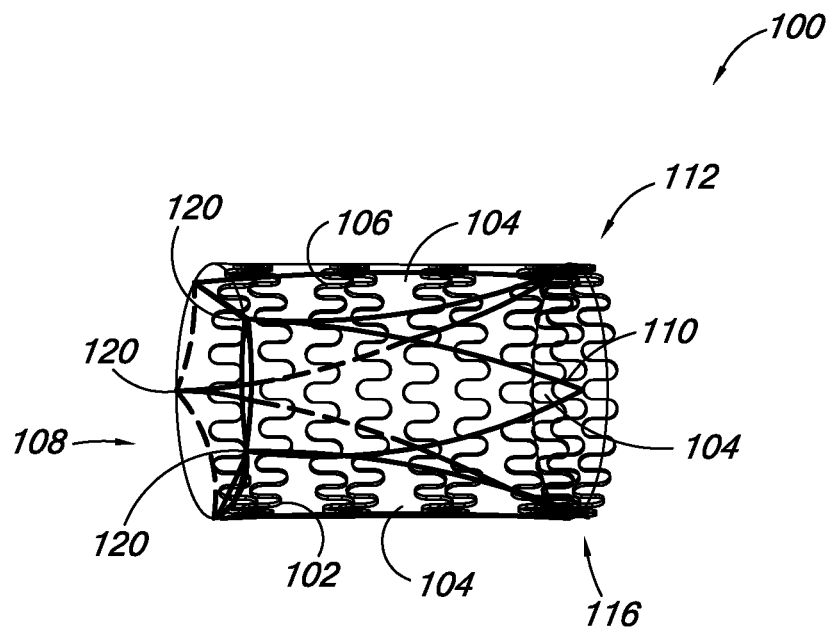

FIGS. 1A and 1B provide an embodiment of a valve 100 of the present disclosure. FIG. 1A illustrates the valve 100 with the valve leaflet 104 in a first position, while FIG. 1B illustrates the valve 100 with the valve leaflet 104 in a second position. The valve 100 includes a valve frame 102 and a valve leaflet 104 coupled to the valve frame 102. The valve frame 102 also includes frame members 106 that define a lumen 108. The valve 100 also includes a leaflet transition member 110 coupled to at least a portion of the valve leaflet 104.

As discussed herein, FIG. 1A illustrates the valve leaflet 104 and leaflet transition member 110 in a first position, where the valve leaflet 104 and leaflet transition member 110 are at least partially outside the lumen 108 of the valve frame 102 and extend away from the lumen 108. The valve leaflet 104 can also include a leaflet frame 111 that is coupled to a portion of the peripheral edge 122 of the valve leaflet 104. In some embodiments, the leaflet frame 111 can have a U-shape, leaving a portion of a distal end 118, relative to the leaflet transition member 110, of the valve leaflet 104 free to move between an open and closed position to function as a valve.

In some embodiments, the leaflet frame 111 can be coupled to the leaflet transition member 110. For example, the leaflet frame 111 can be hinged to the leaflet transition member 110 to allow the leaflet transition member 110 to move inside the leaflet frame 111 and invert the leaflet frame 111 from the first position, as shown in FIG. 1A, to the second position, as shown in FIG. 1B. The valve leaflet 104 can be coupled to the leaflet frame 111 in a variety of ways including sewing, suturing, and/or arc welding, among other methods.

In some embodiments, the valve frame 102 can have an elongate tubular structure with a proximal end 112 and a distal end 114, relative to the leaflet transition member 110. In some embodiments, portions of the frame members 106 can define the proximal and distal ends 112, 114 of the valve frame 102. In addition, the valve leaflet 104 can have a proximal end 116 and a distal end 118, relative to the leaflet transition member 110, where a portion of the distal end 118 of the valve leaflet 104 can be coupled adjacent to the proximal end 112 of the valve frame 102 at junction points 120. As used herein, "junction points" refer to places on the valve frame 102 where the valve leaflet 104 is coupled to the valve frame 102. In some embodiments, the junction points 120 can be located at a number of different positions on the valve frame 102. In some embodiments, the junction points 120 can be located at the same relative position around the valve frame 102. For example, when a valve 100 includes two valve leaflets 104, the junction points 120 can be set opposite each other in a mirror image relationship.

In embodiments where there are more than two leaflets 104, the junction points 120 can be set along the valve frame 102 at positions that are equidistant from each other. This aspect of the disclosure is illustrated in FIG. 1, which shows the valve 100 with three valve leaflets 104 having three junction points 120 set on the valve frame 102 at positions that are equidistant from each other. Alternatively, the junction points 120 can be at different relative locations along the valve frame 102. For the various embodiments, the junction points 120 can be located on the valve frame 102 such that the valve leaflet 104 can transition from a first position as shown in FIG. 1A to a second position shown in FIG. 1B, as will be discussed herein.

As illustrated in FIG. 1A, the valve 100 can include the leaflet transition member 110 coupled to at least a portion of the valve leaflet 104 and/or the leaflet frame 111. In some embodiments, the leaflet transition member 110 can be a ring structure that is coupled to the proximal end 116 of the valve leaflet 104. The leaflet transition member 110 can be expandable from a first diameter to a second diameter. As shown in FIG. 1A, the leaflet transition member 110 in the first position can have the first diameter. In various embodiments, the leaflet transition member 110 can have a serpentine shape in order to allow the leaflet transition member 110 to expand from the first diameter to the second diameter. The leaflet transition member 110 can also have other shapes, for example, the leaflet transition member 110 can include leaflet transition member 110 portions that can form a coil. The coil portions can allow the leaflet transition member 110 to have a first diameter in the first position and expand to a second diameter. The leaflet transition member 110 can also have other shapes.

In some embodiments, the leaflet transition member 110 can be formed of a shape-memory material. Examples of shape-memory materials include shape memory plastics, polymers, thermoplastic materials, and metal-alloys which are inert in the body. Some shape-memory materials, (e.g., nickel-titanium alloys) can be temperature-sensitive and change shape at a designated temperature or temperature range. Shape memory metal-alloys are generally made from nickel and titanium in specific ratios, commonly known as Nitinol. Other materials are also possible.

FIG. 1B provides an embodiment of a valve 100 of the present disclosure when the valve leaflets 104 and leaflet frame 110 are in the second position. As illustrated, the valve leaflet 104 and leaflet transition member 110 can transition from the first position to the second position by pivoting the valve leaflet 104 inside the valve frame 102 at the junction points 120. In the second position, the proximal end 116 of the valve leaflet 104 and at least a portion of the leaflet transition member 110 are within the lumen 108 of the valve frame 102. In some embodiments, the leaflet transition member 110 in the second position can be coupled adjacent to the distal end 114 of the valve frame 102, for example, the leaflet transition member 110 can be coupled to frame members 106 on the distal end 114 of the valve frame 102.

As discussed herein, the leaflet transition member 110 can expand from a first diameter to a second diameter. The leaflet transition member 110 can expand to the second diameter to secure the leaflet frame 110 to the valve frame 102 and/or to secure the leaflet transition member 110 in the second position. As illustrated in FIG. 1B, the leaflet transition member 110 can have a serpentine shape to allow the leaflet transition member 110 to expand, however, the serpentine shape can also allow portions of the leaflet transition member 110 to expand through the valve frame 102 and between the frame members 106. By expanding through the valve frame 102 and between the frame members, the leaflet transition member 110 can be held in the second position.

For the various embodiments, the valve frame 102 can be formed of a balloon expandable material, as discussed herein. The valve frame 102 can also be formed of a material with a spring bias. The valve frame 102 can also be a shape memory material, as discussed herein. Other materials are also possible.

For the various embodiments, the frame members 106 and/or the leaflet transition member 110 can have similar and/or different cross-sectional geometries along their length. The similarity and/or the differences in the cross-sectional geometries can be selected based on one or more desired functions to be elicited from each portion of the valve frame 102. Examples of cross-sectional geometries include rectangular, non-planar configuration (e.g., bent), round (e.g., circular, oval, and/or elliptical), polygonal, arced, and tubular. Other cross-sectional geometries are possible.

The valve 100 can further include one or more radiopaque markers (e.g., tabs, sleeves, welds). For example, one or more portions of the valve frame 102 can be formed from a radiopaque material. Radiopaque markers can be attached to and/or coated onto one or more locations along the valve frame 102. Examples of radiopaque material include, but are not limited to, gold, tantalum, and platinum. The position of the one or more radiopaque markers can be selected so as to provide information on the position, location, and orientation of the valve 100 during its implantation.

The valve 100 further includes the leaflets 104 having surfaces defining a reversibly sealable opening for unidirectional flow of a liquid through the valve 100. Each of the valve leaflets 104 are coupled to the valve frame 102, where the leaflets 104 can repeatedly move between an open state and a closed state for unidirectional flow of a liquid through a lumen of the valve 100. For example, the leaflets 104 can be coupled to the proximal end 112 of the valve frame 102 so as to span and control fluid flow through the lumen 108 of the valve 100. For the present embodiment, the valve 100 includes three of the valve leaflets 104 for a tri-leaflet configuration. As appreciated, mono-leaflet, bi-leaflet and/or other multi-leaflet configurations are also possible.

In some embodiments, the leaflets 104 can be derived from autologous, allogeneic or xenograft material. As will be appreciated, sources for xenograft material (e.g., cardiac valves) include, but are not limited to, mammalian sources such as porcine, equine, and sheep. Additional biologic materials from which to form the valve leaflets 104 include, but are not limited to, explanted veins, pericardium, facia lata, harvested cardiac valves, bladder, vein wall, various collagen types, elastin, intestinal submucosa, and decellularized basement membrane materials, such as small intestine submucosa (SIS), amniotic tissue, or umbilical vein.

Alternatively, the leaflets 104 can be formed from a synthetic material. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), polyester, polyethylene (PE), polyethylene terephthalate (PET), silk, urethane, Rayon, Silicone, or the like. In an additional embodiment, the synthetic material can also include metals, such as stainless steel (e.g., 316L) and nitinol. These synthetic materials can be in a woven, a knit, a cast or other known physical fluid-impermeable or permeable configurations. In addition, gold plated metals can be embedded in the leaflet 104 material (e.g., a sandwich configuration) to allow for visualization of the leaflets 104 post placement.

As will be appreciated, the valve 100 can be treated and/or coated with any number of surface or material treatments. Examples of such treatments include, but are not limited to, bioactive agents, including those that modulate thrombosis, those that encourage cellular ingrowth, throughgrowth, and endothelialization, those that resist infection, and those that reduce calcification.

Figure 2A:
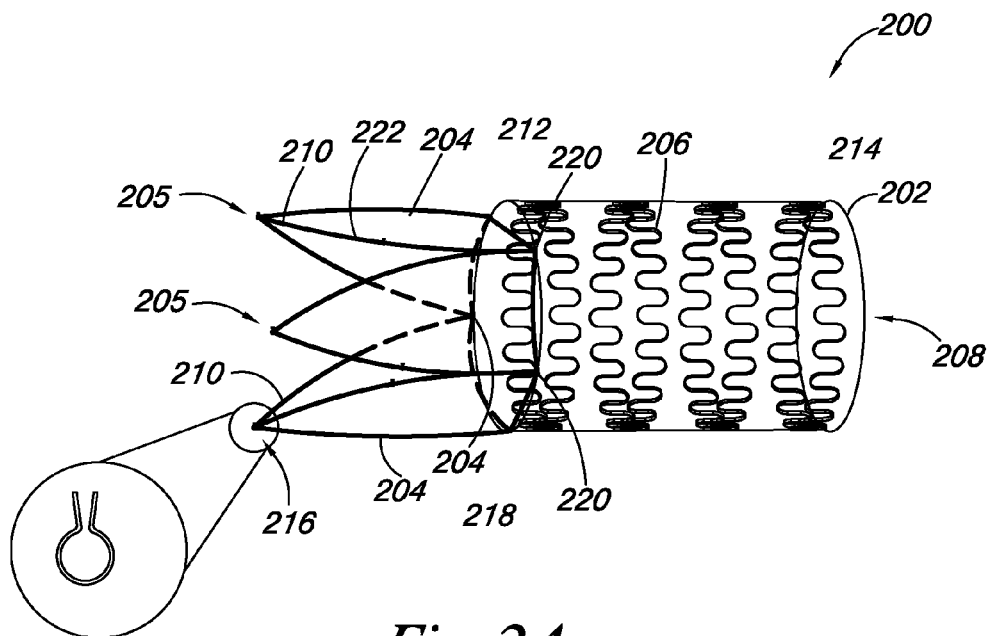
FIGS. 2A-2B provide an embodiment of a valve of the present disclosure.
Figure 2B:
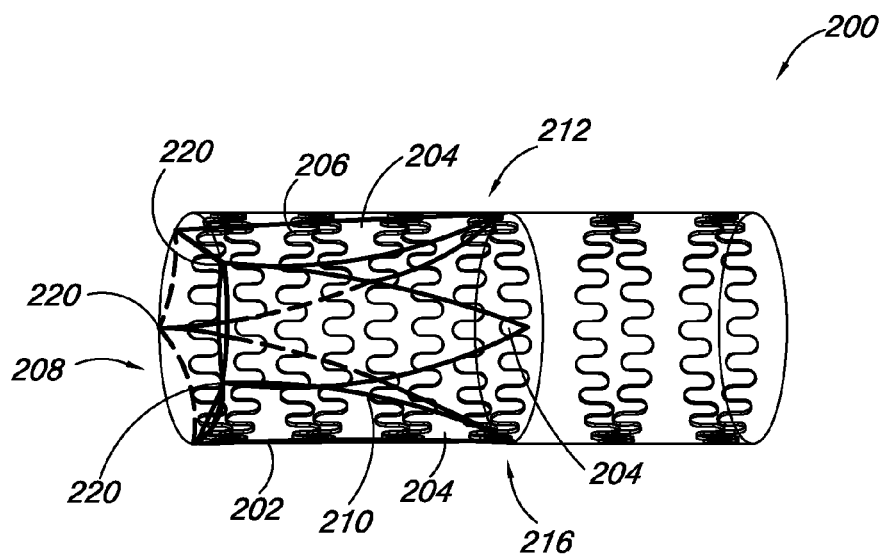

FIGS. 2A and 2B provide an embodiment of a valve 200 of the present disclosure. As discussed herein, the valve 200 includes a valve frame 202 and a valve leaflet 204 coupled to the valve frame 202. The valve frame 202 also includes frame members 206 that define a lumen 208. As shown in FIGS. 2A and 2B, the valve leaflets 204 can include a leaflet frame 211, as discussed herein, coupled to at least a portion of the peripheral edge 222 of the valve leaflets 204. In such embodiments, the leaflet frame 211 can act as the leaflet transition member 210.

FIG. 2A illustrates the valve leaflet 204 and leaflet transition member 210 (i.e., leaflet frame 211) in a first position, where the valve leaflet 204 and leaflet transition member 210 are at least partially outside the lumen 208 of the valve frame 202 and extend away from the lumen 208. FIG. 2B illustrates the valve 200 where the valve leaflet 204 and leaflet transition member 210 are in a second position within the lumen 208 of the valve frame 202, as discussed herein.

As shown in FIGS. 2A and 2B, in some embodiments, the leaflet frame 211 can be coupled to a portion of a peripheral edge 222 of the valve leaflet 204. In such embodiments, the leaflet frame 211 can form the outside boundary of a portion of the valve leaflet 204 and can hold the valve leaflet 204 in a desired position. As discussed herein, the valve leaflet 204 can have a proximal end 216 and a distal end 218, where a portion of the distal end 218 of the valve leaflet 204 can be coupled adjacent to the proximal end 212 of the valve frame 202 at junction points 220. In some embodiments, the valve leaflet 204 can be coupled to the valve frame 202 such that the valve leaflet 204 can pivot inside the valve frame 302 at the junction points 220.

In other embodiments, the leaflet transition member 210 (i.e., leaflet frame 211) can be coupled to the peripheral edge 222 of the valve leaflet 204 such that the leaflet transition member 210 is coupled to the proximal end 212 of the valve frame 202. In such embodiments, the leaflet transition member 210 can be hinged to a portion of the valve frame 202 to couple the valve frame 202 and the valve leaflet 204. Also, hinging the leaflet transition member 210 to the valve frame 202 can allow the leaflet transition member 210 and the valve leaflet 204 to transition from the first position to the second position, as shown in FIGS. 2A and 2B.

In addition, as discussed herein, the leaflet transition member 210 can be coupled to the valve frame 202 to hold the leaflet frame 210 in the second position. In such embodiments, the leaflet transition member 210 can include mechanical members 205 to hold the leaflet transition member 210 to the frame members 206 of the valve frame 202. One embodiment of a mechanical member 205 is shown in FIG. 2A as a close-up view. In this embodiment, the mechanical member 205 can be in the form of a clip, where a frame member 206 can slide into the clip 205 to secure the leaflet frame 210 to the valve frame 202. In another embodiment, the mechanical member 205 can be a hook that hooks the leaflet transition member 210 to the frame members in several different locations. Other mechanical member 205 configurations are also possible.

Figure 3A:
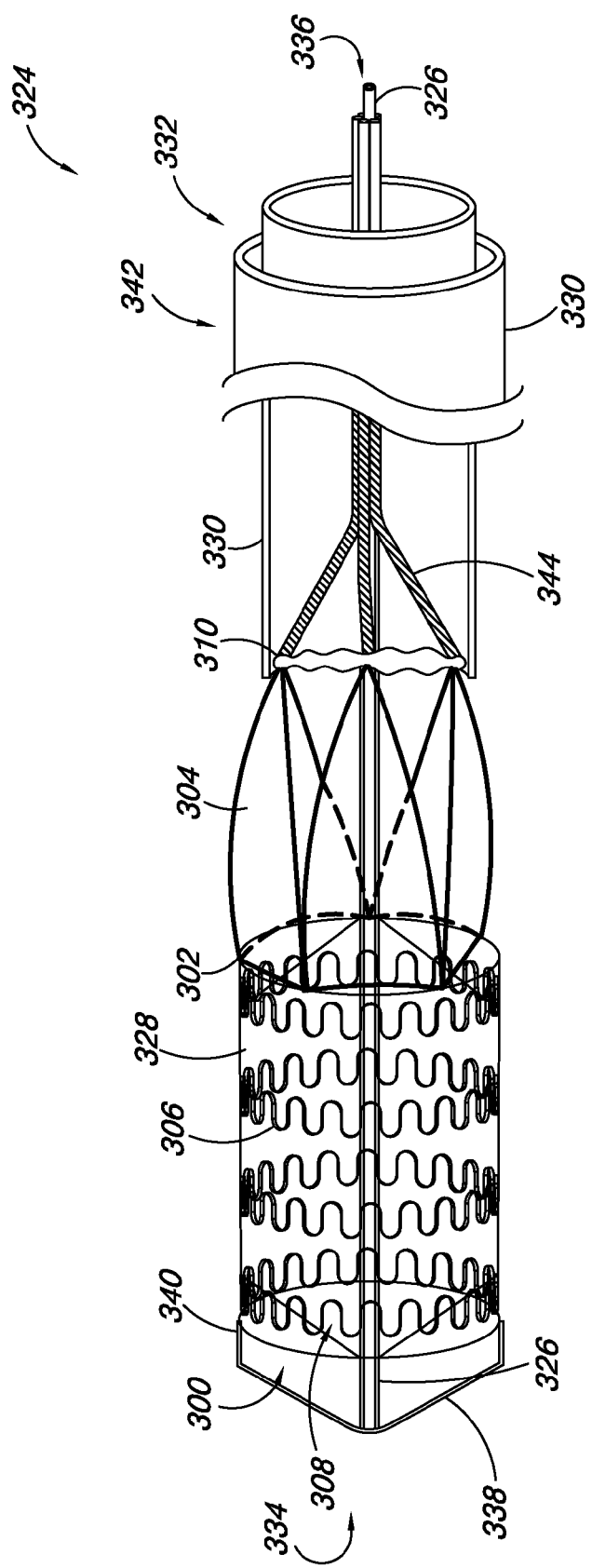
FIGS. 3A-3C illustrate an embodiment of a system according to the present disclosure.
Figure 3B:
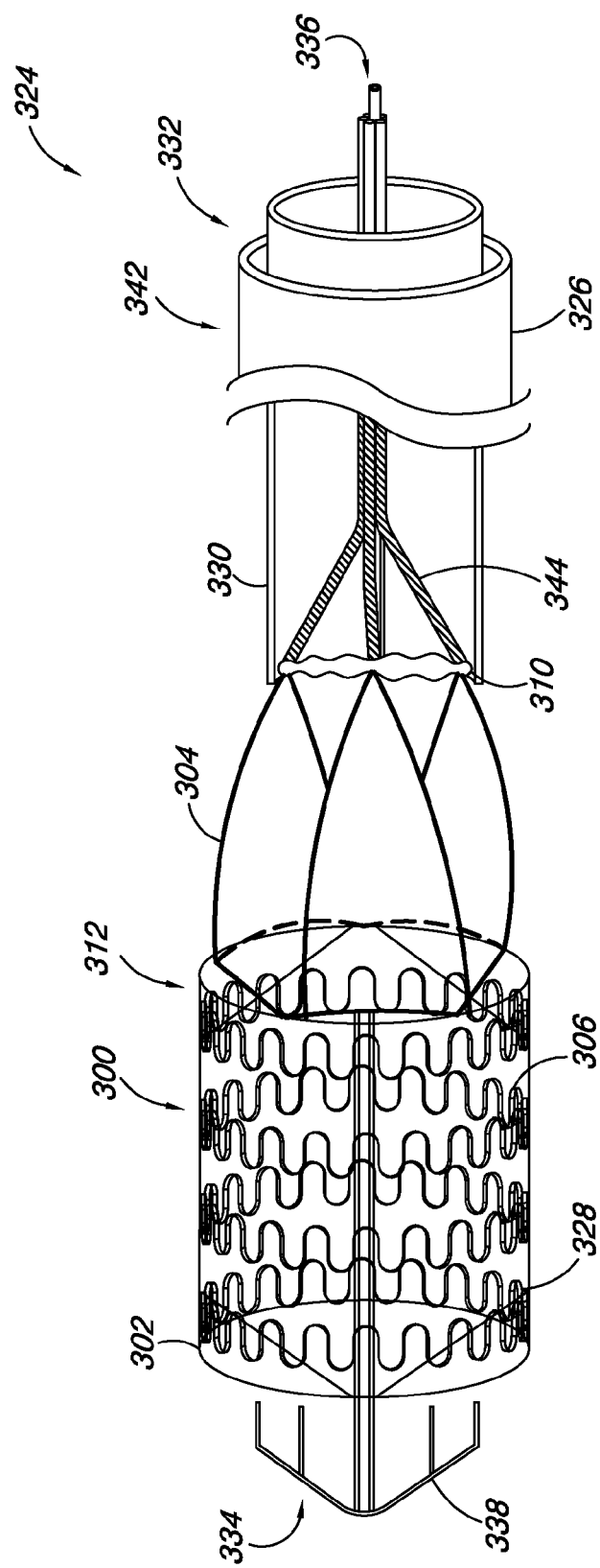
Figure 3C:
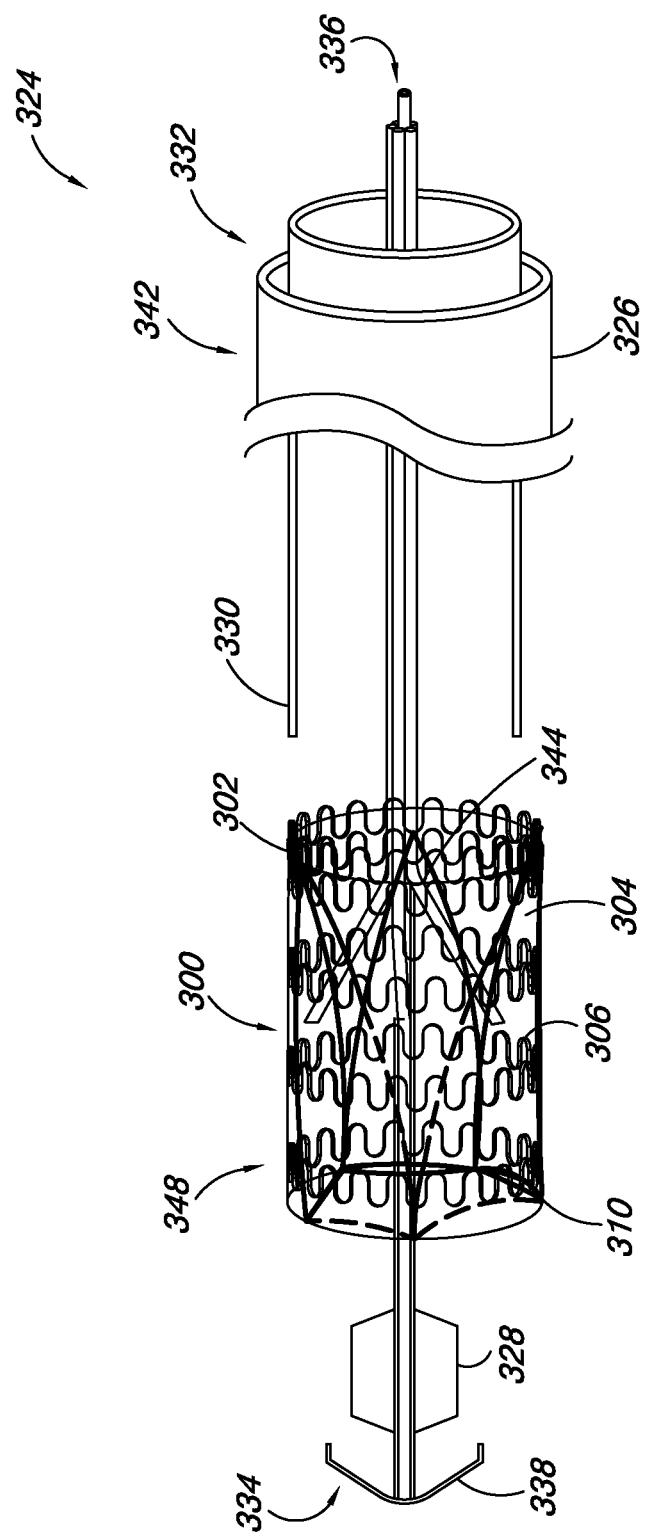

FIGS. 3A-3C illustrate an embodiment of a system 324 according to the present disclosure. The system 324 includes a valve 300, as described herein, releasably joined to an elongate delivery catheter 326 and an expandable balloon 328 positioned around at least a portion of the elongate delivery catheter 326. The system 324 also includes a retractable sheath 330 positioned around at least a portion of the elongate delivery catheter 326. Also, a portion of the valve 300 is positioned between the elongate delivery catheter 326 and the retractable sheath 330. For example, FIG. 3A illustrates an embodiment in which the retractable sheath 330 is positioned around at least a portion of the delivery catheter 326 to releasably hold the leaflet transition member 310 in a delivery state.

In some embodiments, the retractable sheath 330 can be positioned such that the retractable sheath holds the valve frame 302 and the leaflet transition member 310 in a delivery state. In such embodiments, the retractable sheath 330 can be partially retracted to allow the valve frame 302 to radially expand while holding the leaflet transition member 310 in the delivery state. FIG. 3B illustrates an embodiment in which valve 300 has expanded to its deployed state, as discussed herein.

In the embodiments illustrated in FIGS. 3A-3C, the delivery catheter 326 includes an elongate body having a proximal end 332 and a distal end 334. A catheter lumen 336 can extend through the proximal and distal ends 332, 334. In some embodiments, the catheter lumen 336 can receive a guidewire for guiding the placement of the valve 300 in the vasculature.

In some embodiments, the elongate delivery catheter 326 can include a distal tip 338. The distal tip 338 can have a conical configuration, where the tip 338 diameter decreases in size to a point at the distal end 334 of the elongate delivery catheter 326.

In addition, in such embodiments, the retractable sheath 330 can move longitudinally (e.g., slide) relative the delivery catheter 326 to allow the valve 300 to radially expand from its delivery state to its deployed state. In some embodiments, moving the retractable sheath 330 relative the delivery catheter 326 can be accomplished by pulling a proximal end 342 of the sheath 330 relative a proximal end 332 of the delivery catheter 326.

FIG. 3B illustrates an embodiment where the valve 300 has been radially expanded. In some embodiments, the valve 300 can be balloon expandable. In other embodiments, the retractable sheath 330, if positioned over the valve frame 302, can be retracted relative the valve 300 to allow the valve 300 to be radially expanded using the expandable balloon 328. In such embodiments, the elongate delivery catheter 326 can include a lumen fluidly attached to the expandable balloon 328 to allow the balloon 328 to be filled with fluid to radially expand the balloon 328, and thus the valve 300.

In some embodiments, the valve 300 can be formed of a material with a spring bias, where the valve 300 can expand when the sheath 330 has been removed. In such embodiments, the expandable balloon 328 can be used to position the valve 300 and/or secure the valve 300 inside a body lumen. Examples of materials with a spring bias can include, but are not limited to, medical grade stainless steel (e.g., 316L), titanium, tantalum, platinum alloys, niobium alloys, cobalt alloys, alginate, or combinations thereof.

In some embodiments, the expandable balloon 328 can be a perfusion balloon. A perfusion balloon can be used to radially expand the valve frame 302 while allowing fluid, for example, blood, to pass through the delivery catheter 326 and valve 300 while the valve 300 is being positioned in the vasculature.

In the embodiment illustrated in FIGS. 3A-3C, the valve 300 includes a valve frame 302 having frame members defining a lumen 308, a valve leaflet 304 attached to a portion of the valve frame 302, and a leaflet transition member 310 attached to at least a portion of the valve leaflet 304. FIG. 3A illustrates an embodiment where the valve leaflet 304 and leaflet transition member 310 are in a first position extending away from the lumen 308 of the valve 300. Although the embodiments illustrated in FIGS. 3A-3C show a valve 300 including a leaflet transition member 310 and a leaflet frame 311, the present disclosure includes embodiments where the leaflet frame 311 acts as the leaflet transition member 310, as discussed herein.

To transition the valve leaflets 304 and leaflet transition member 310 from the first position to a second position within the lumen 308 of the valve frame 302, the elongate delivery catheter 326 can include a number of elongate push members 344 releasably coupled to the leaflet transition member 310. The elongate push members 344 can be positioned around the elongate delivery catheter 326, and can be used to push the leaflet transition member 310 inside the lumen 308 of the valve 300.

In some embodiments, the elongate push members 344 can move in a longitudinal direction relative the elongate delivery catheter 326. The elongate push members 344 can be formed of a plastic material, where the elongate push members 344 are moved into the lumen 308 of the valve 300 to push the leaflet transition member 310 and the valve leaflet 304 from the first position to the second position. The elongate push members 344 can also be formed of different materials. For example, the elongate push members 344 can be formed of a wire or thread releasably attached to the leaflet transition member 310. As such, as the elongate push members 344 are moved into the lumen 308 of the valve 300, the elongate push members 344 would pull the leaflet transition member 310 and the valve leaflet 304 from the first position to the second position. Other methods of transitioning the leaflet transition member 310 and the valve leaflet 304 from the first position to the second position are also possible.

As discussed herein, FIG. 3B illustrates an embodiment where the valve frame 302 is radially expanded. Also shown is how the leaflet transition member 310 can remain in a contracted state while the valve frame 302 is expanded. In some embodiments, the leaflet transition member 310 can be formed of a shape-memory material, such as a nickel-titanium alloy, where the leaflet transition member 310 and/or leaflet frame 311 is restrained in a contracted state by the retractable sheath 330.

In some embodiments, the leaflet transition member 310 is formed of a shape memory material, as discussed herein. In such embodiments, the retractable sheath 330 can be used to hold the leaflet transition member 310 in the first position while the valve frame 302 is radially expanded.

FIG. 3B also illustrates how a portion of the leaflet frame 311 can expand when the valve frame 302 is radially expanded. In some embodiments, the leaflet frame 311 can be coupled to the proximal end 312 of the valve frame 302 such that when the valve frame 302 is radially expanded, the leaflet frame 311 is coupled to the valve frame 302 at junction points 320 that are equidistant apart, as discussed herein.

In addition, in some embodiments, the leaflet frame 311 can be formed of a shape memory material to allow the leaflet frame 311 to deform when the valve frame 302 is expanded and the leaflet transition member 310 is held in the delivery state. In such embodiments, once the valve frame 302 is expanded and the valve leaflet 304 and leaflet transition member 310 are in the second position, the leaflet frame 311 can transition to a deployed state to hold the valve leaflet 304 in a position to act as a valve.

As discussed herein, the number of elongate push members 344 can be used to push the leaflet transition member 310 inside the lumen 308 of the valve frame 302 to place the valve leaflet 304 and leaflet transition member 310 into the second position. Once the leaflet transition member 310 is inside the lumen 308, the leaflet transition member 310 can be radially expanded inside the valve frame 302 and the number of elongate members 344 can be released from the leaflet transition member 310. In some embodiments, the leaflet transition member 310 can be formed of a material with a spring bias, as discussed herein, and expand when the retractable sheath 330 is retracted relative the valve 300 to release the leaflet transition member 310 while the elongate push members 344 hold the leaflet transition member 310 in place within the lumen 308 of the valve 300. Once the leaflet transition member 310 is expanded, the elongate push members 344 and the delivery catheter 326 can be retracted through the valve 300.

Alternatively, in embodiments where the leaflet transition member 310 is formed of a shape memory material, the leaflet frame 310 can radially expand when the retractable sheath 330 is retracted relative the valve 300 and the leaflet transition member 310 warms to a certain temperature, for example, at or below normal body temperature (e.g., 37 degrees Celsius).

FIG. 3C illustrates an embodiment of the valve frame 302 radially expanded, where the valve leaflet 304 and leaflet transition member 310 are in the second position. As illustrated, once the leaflet transition member 310 and the valve frame 302 are expanded, the expandable balloon 328 and distal tip 338 can be retracted through the lumen 308 of the valve frame 302.

In some embodiments, the leaflet transition member 310 can be secured to the valve frame 302 once the leaflet transition member 310 is in the second position and both the leaflet transition member 310 and the valve frame 302 are radially expanded. For example, as discussed herein, the leaflet transition member 310 can expand from a first diameter to a second diameter where portions of the leaflet transition member 310 extend through the valve frame 302 and between the frame members 306 to secure the leaflet transition member 310 in the second position. In other embodiments, the leaflet transition member 310 and/or leaflet frame 311 can include mechanical members, as discussed herein, to secure the leaflet transition member 310 and/or leaflet frame 311 to the valve frame 302. A combination of mechanical members and expanding the leaflet transition member 310 to extend portions of the leaflet transition member 310 through the valve frame 302 and between the frame members 306 is also possible.

Embodiments of the system 324 can further include an expandable filter that forms a portion of the retractable sheath. Examples of such an embodiment can be found in U.S. Provisional Patent application 60/899,444 and co-pending U.S. patent application Ser. No. 12/012,911 entitled "Percutaneous Valve, System and Method", both of which are hereby incorporated by reference in their entirety.

Each of the delivery catheter 326, the retractable sheath 330, and/or the second retractable sheath 346 can be formed of a number of materials. Materials include polymers, such as PVC, PE, POC, PET, polyamide, mixtures, and block co-polymers thereof. In addition, each of the delivery catheter 326, the retractable sheath 330, and/or the second retractable sheath 346 can have a wall thickness and an inner diameter sufficient to allow the structures to slide longitudinally relative each other, as described herein, and to maintain the valve 300 in a delivery state, as discussed herein.

In an additional embodiment, the valve 300 can further include a sealing material 348 positioned on the periphery of the valve frame 302. In one embodiment, once implanted the sealing material 348 can swell due the presence of liquid to occupy volume between the valve frame 302 and the tissue on which the valve 300 has been implanted so as to prevent leakage of the liquid around the outside of the valve 300.

Embodiments can also include a sealing material positioned on a portion of the peripheral edge 322 of the leaflet frame 311 to seal the leaflet frame 311 to the valve frame 302.

A variety of suitable materials for the sealing material 348 are possible. For example, the sealing material 348 can be selected from the general class of materials that include polysaccharides, proteins, and biocompatible gels. Specific examples of these polymeric materials can include, but are not limited to, those derived from poly(ethylene oxide) (PEO), poly(ethylene glycol) (PEG), poly(vinyl alcohol) (PVA), poly(vinylpyrrolidone) (PVP), poly(ethyloxazoline) (PEOX) polyaminoacids, pseudopolyamino acids, and polyethyloxazoline, as well as copolymers of these with each other or other water soluble polymers or water insoluble polymers. Examples of the polysaccharide include those derived from alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives, and carrageenan. Examples of proteins include those derived from gelatin, collagen, elastin, zein, and albumin, whether produced from natural or recombinant sources.

In an additional embodiment, the valve 300 of the present disclosure can include anchoring members attached to the valve frame 302 or frame members 306. Anchoring members can include barbs, hooks, etc.

The embodiments of the valve described herein may be used to replace, supplement, or augment valve structures within one or more lumens of the body. For example, embodiments of the present invention may be used to replace an incompetent cardiac valve of the heart, such as the aortic, pulmonary and/or mitral valves of the heart. In one embodiment, the native cardiac valve can either remain in place or be removed (e.g., via a valvoplasty procedure) prior to implanting the cardiac valve of the present disclosure.

In addition, positioning the system having the valve as discussed herein includes introducing the system into the cardiovascular system of the patient using minimally invasive percutaneous, transluminal techniques. For example, a guidewire can be positioned within the cardiovascular system of a patient that includes the predetermined location. The system of the present disclosure, including the valve as described herein, can be positioned over the guidewire and the system advanced so as to position the valve at or adjacent the predetermined location. In one embodiment, radiopaque markers on the catheter and/or the valve, as described herein, can be used to help locate and position the valve.

The valve can be deployed from the system at the predetermined location in any number of ways, as described herein. In one embodiment, valve of the present disclosure can be deployed and placed in any number of cardiovascular locations. For example, valve can be deployed and placed within a major artery of a patient. In one embodiment, major arteries include, but are not limited to, the aorta. In addition, valves of the present invention can be deployed and placed within other major arteries of the heart and/or within the heart itself, such as in the pulmonary artery for replacement and/or augmentation of the pulmonary valve and between the left atrium and the left ventricle for replacement and/or augmentation of the mitral valve. Other locations are also possible.

Once implanted, the valve can provide sufficient contact with the body lumen wall to prevent retrograde flow between the valve and the body lumen wall, and to securely located the valve and prevent migration of the valve. The valve described herein also displays sufficient flexibility and resilience so as to accommodate changes in the body lumen diameter, while maintaining the proper placement of valve. As described herein, the valve can engage the lumen so as to reduce the volume of retrograde flow through and around valve. It is, however, understood that some leaking or fluid flow may occur between the valve and the body lumen and/or through valve leaflets.

Embodiments of the present disclosure also include a valve that includes a valve frame having a lumen; a valve leaflet attached to a portion of the valve frame; a leaflet transition member attached to at least a portion of the valve leaflet, where the valve leaflet and leaflet transition member extend away from the lumen in a first position and transition into a second position in which the valve leaflet and leaflet transition member are inside the lumen of the valve frame. For the embodiments of the valve, the leaflet transition member in the second position is coupled to the frame members. For the embodiments of the valve, the leaflet transition member expands from a contracted state in the first position to an expanded state in the second position. For the embodiments of the valve, the leaflet transition member has a serpentine shape in the contracted state in order to expand from a first diameter to a second diameter in the expanded state. For the embodiments of the valve thee valve frame includes frame members defining the lumen and the leaflet transition member in the expanded state includes at least a portion of the leaflet transition member that is expanded between the frame members to secure the leaflet transition member in the second position.

Embodiments of the present disclosure also include a structure for forming a valve that include a valve frame having a distal end and a proximal end, and frame members defining a lumen; a valve leaflet having a distal end and a proximal end, where a portion of the distal end of the valve leaflet is coupled adjacent to the proximal end of the valve frame; and a leaflet transition member coupled to at least a portion of the valve leaflet, where the valve leaflet and the leaflet transition member in a first position are at least partially outside the lumen of the valve frame with the proximal end of the valve leaflet extending away from both the distal end and the proximal end of the valve frame.

For the embodiments of the structure, the valve leaflet and leaflet transition member transition from the first position to a second position in which the proximal end of the leaflet and at least a portion of the leaflet transition member are within the lumen of the valve frame. For the embodiments of the structure, the leaflet transition member is a ring structure coupled to the proximal end of the valve leaflet. For the embodiments of the structure, the valve leaflet includes a leaflet frame coupled to a portion of a peripheral edge of the valve leaflet, and the leaflet transition member is coupled to the leaflet frame.

While the present invention has been shown and described in detail above, it will be clear to the person skilled in the art that changes and modifications may be made without departing from the spirit and scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled. In addition, one of ordinary skill in the art will appreciate upon reading and understanding this disclosure that other variations for the invention described herein can be included within the scope of the present invention.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A valve, comprising:
   a valve frame having a distal end and a proximal end, and frame members defining an lumen;
   a valve leaflet having a distal end and a proximal end, wherein a portion of the distal end of the valve leaflet is coupled adjacent to the proximal end of the valve frame; and
   a leaflet transition member coupled to at least a portion of the valve leaflet; and
   at least one mechanical member engaged to the leaflet transition member,
   wherein, in a first position, the valve leaflet and the leaflet transition member are at least partially outside the lumen of the valve frame with the proximal end of the valve leaflet extending away from both the distal end and the proximal end of the valve frame,
   wherein the valve leaflet and the leaflet transition member transition from the first position to a second position in which the proximal end of the valve leaflet and at least a portion of the leaflet transition member are within the lumen of the valve frame, and
   wherein, in the second position, the at least one mechanical member is coupled to the valve frame.

2. The valve of claim 1, wherein the at least one mechanical member is a clip.

3. The valve of claim 1, wherein the at least one mechanical member is a hook.

4. The valve of claim 1, wherein the leaflet transition member is expandable from a first diameter to a second diameter.

5. The valve of claim 4, wherein the leaflet transition member has the first diameter in the first position and the leaflet transition member expands to the second diameter in the second position.

6. The valve of claim 1, wherein the valve leaflet includes a leaflet frame coupled to a portion of a peripheral edge of the valve leaflet.

7. The valve of claim 6, wherein the leaflet frame acts as the leaflet transition member.

8. A method for deployment of a valve, comprising:
   radially expanding a valve frame of the valve from a deliver state to a deployed state;
   transitioning a leaflet transition member coupled to a valve leaflet in a first position outside a lumen of the valve frame to a second position inside the lumen of the valve frame; and
   coupling, in the second position, at least one mechanical member to the valve frame,
   wherein the at least one mechanical member is engaged to the leaflet transition member.

9. The method of claim 8, wherein transitioning the leaflet transition member in the first position outside the lumen of the valve frame to the second position inside the lumen of the valve frame comprises releasing the leaflet transition member from the first position.

10. The method of claim 9, further comprising pushing the leaflet transition member in the first position from outside the lumen to the inside of the lumen of the valve frame.

11. A system, comprising:
    an elongate delivery catheter;
    an expandable balloon positioned around at least a portion of the elongate delivery catheter;
    a retractable sheath positioned around at least a portion of the elongate delivery catheter, wherein the retractable sheath moves longitudinally relative the elongate delivery catheter; and
    a valve, wherein a portion of the valve is positioned between the elongate delivery catheter and the retractable sheath, and wherein the valve comprises:
    a valve frame having a distal end and a proximal end, and frame members defining an lumen;
    a valve leaflet having a distal end and a proximal end, wherein a portion of the distal end of the valve leaflet is coupled adjacent to the proximal end of the valve frame; and
    a leaflet transition member coupled to at least a portion of the valve leaflet; and
    at least one mechanical member engaged to the leaflet transition member,
    wherein, in a first position, the valve leaflet and the leaflet transition member are at least partially outside the lumen of the valve frame with the proximal end of the valve leaflet extending away from both the distal end and the proximal end of the valve frame,
    wherein the valve leaflet and the leaflet transition member transition from the first position to a second position in which the proximal end of the valve leaflet and at least a portion of the leaflet transition member are within the lumen of the valve frame, and
    wherein, in the second position, the at least one mechanical member is coupled to the valve frame.

12. The system of claim 11, wherein the at least one mechanical member is a clip.

13. The system of claim 11, wherein the at least one mechanical member is a hook.

14. The system of claim 11, wherein the portion of the valve positioned between the elongate delivery catheter and the retractable sheath is the leaflet transition member and a portion of the valve leaflet.

15. The system of claim 14, wherein the retractable sheath restrains the leaflet transition member in the first position.

16. The system of claim 11, further comprising a plurality of elongate push members releasably coupled to the leaflet transition member wherein the elongate push members transition the leaflet transition member and the valve leaflet from the first position to the second position.

17. The system of claim 11, wherein the valve leaflet includes a leaflet frame coupled to a portion of a peripheral edge of the valve leaflet.

18. The system of claim 17, wherein the leaflet frame is hinged to a portion of the valve frame to couple the valve frame and valve leaflet.

\* \* \* \* \*